United States Patent
Bystrom et al.

(10) Patent No.: US 10,466,260 B2
(45) Date of Patent: Nov. 5, 2019

(54) HDL-ASSOCIATED PROTEIN EXTRACTION AND DETECTION

(71) Applicant: Cleveland HeartLab, Inc., Cleveland, OH (US)

(72) Inventors: Cory Bystrom, Beachwood, OH (US); Timothy Collier, Cleveland, OH (US)

(73) Assignee: Cleveland Heartlab, Inc., Cleveland, OH (US)

( * ) Notice: Subject to any disclaimer, the term of this patent is extended or adjusted under 35 U.S.C. 154(b) by 0 days.

(21) Appl. No.: 15/788,876

(22) Filed: Oct. 20, 2017

(65) Prior Publication Data

US 2018/0031586 A1 Feb. 1, 2018

Related U.S. Application Data

(62) Division of application No. 14/858,111, filed on Sep. 18, 2015, now Pat. No. 9,810,702.

(60) Provisional application No. 62/052,854, filed on Sep. 19, 2014.

(51) Int. Cl.
*A61K 38/00* (2006.01)
*G01N 33/92* (2006.01)

(52) U.S. Cl.
CPC ....... *G01N 33/92* (2013.01); *G01N 2333/775* (2013.01)

(58) Field of Classification Search
None
See application file for complete search history.

(56) References Cited

U.S. PATENT DOCUMENTS

| 8,343,932 B2 * | 1/2013 | Eyckerman .......... C07K 14/775 435/18 |
| 2010/0129828 A1 * | 5/2010 | Beaulieu .......... G01N 33/57419 435/7.1 |
| 2013/0017556 A1 | 1/2013 | Prtichard, Jr. et al. |
| 2016/0084856 A1 | 3/2016 | Bystrom et al. |

OTHER PUBLICATIONS

Gupta, Protein Expression and Purification 39 (2005) 261-268 (Year: 2005).*
Website: https://web.archive.org/web/20140522220448/https://www.neb.conn/tools-and-resources/ . . . (Year: 2013).*
Calvete, FEBS Letters 444, (1999) 260-264 (Year: 1999).*
Bergt et al., The myeloperoxidase product hypochlorous acid oxidizes HDL in the human artery wall and impairs ABCA1-dependent cholesterol transport, Proc Natl Acad Sci U S A. Aug. 31, 2004;101(35):13032-7.
Davidsson et al., Proteomics of apolipoproteins and associated proteins from plasma high-density lipoproteins. Arterioscler Thromb Vasc Biol. Feb. 2010;30(2):156-63.
Google Search, HDL Associated Proteins, retrieved Dec. 8, 2016, 2 pages.
Huang et al. , An abundant dysfunctional apolipoprotein A1 in human atheroma, Nat Med. Feb. 2014;20(2):193-203.
Shao et al., Myeloperoxidase targets apolipoprotein A-I, the major high density lipoprotein protein, for site-specific oxidation in human atherosclerotic lesions, J Biol Chem. Feb. 24, 2012;287(9):6375-86.

* cited by examiner

*Primary Examiner* — Satyanarayana R Gudibande
(74) *Attorney, Agent, or Firm* — Foley & Lardner LLP

(57) ABSTRACT

Provided herein are compositions, systems, and methods for extracting and detecting at least one HDL-associated protein (e.g., ApoA1) from a sample (e.g., plasma or serum sample). In certain embodiments, a strong organic acid and hydrophilic organic solvent are mixed with the sample; after centrifugation, the supernatant is transferred to a second container where it is mixed with a non-polar organic solvent; after centrifugation, the lower aqueous layer is transferred to a third container; and then at least a portion of the transferred aqueous layer is subjected to a detection assay such that at least one HDL-associated protein is detected.

16 Claims, 5 Drawing Sheets

Specification includes a Sequence Listing.

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial sequence
<220> FEATURE:
<223> OTHER INFORMATION: Synthetic

<400> SEQUENCE: 1

Glu Asn Gly Gly Ala Arg Leu Ala Glu Tyr Tyr His Ala Lys
1               5                   10

<210> SEQ ID NO 2
<211> LENGTH: 18
<212> TYPE: PRT
<213> ORGANISM: Artificial sequence
<220> FEATURE:
<223> OTHER INFORMATION: Synthetic

<400> SEQUENCE: 2

Leu Arg Glu Gln Leu Gly Pro Val Thr Gln Glu Phe Trp Asp Asn Leu
1               5                   10                  15

Glu Lys
```

HDL-ASSOCIATED PROTEIN EXTRACTION AND DETECTION

CROSS-REFERENCE TO RELATED APPLICATIONS

The present invention is a divisional of U.S. patent application Ser. No. 14/858,111, filed Sep. 18, 2015, which claims priority benefit from U.S. Provisional Patent Application 62/052,854, filed Sep. 19, 2014, each of which is incorporated by reference in its entirety.

FIELD OF THE INVENTION

Provided herein are compositions, systems, and methods for extracting and detecting at least one HDL-associated protein (e.g., ApoA1) from a sample (e.g., plasma or serum sample). In certain embodiments, a strong organic acid and hydrophilic organic solvent are mixed with the sample; after centrifugation, the supernatant is transferred to a second container where it is mixed with a non-polar organic solvent; after centrifugation, the lower aqueous layer is transferred to a third container; and then at least a portion of the transferred aqueous layer is subjected to a detection assay such that at least one HDL-associated protein is detected.

BACKGROUND

Serum lipoproteins comprise a heterogeneous population of lipid-protein complexes that can be grouped into broad classes, very low (VLDL), low (LDL) and high (HDL) density, based on differences in particle density related to lipid and protein content. VLDL and LDL are composed of predominately lipid, while high density lipoproteins have a higher content of protein (about 50%). The density of LDL is between 1.006-1.063 g/ml while that of HDL and HDL-like particles is 1.063-1.21 g/ml. Classical methods to separate HDL from VLDL and LDL employ sequential density ultracentrifugation using potassium bromide salt solutions prepared with densities in the range of each lipoprotein class. One drawback of these methods for the preparation of purified HDL is that they require a minimum of two prolonged ultracentrifugation steps. The first step, which isolates VLDL and LDL from HDL, requires an 18 hour ultracentrifugation spin in d=1.063 g/ml KBr salt solution. The buoyant VLDL and LDL are concentrated in the upper layers of the salt gradient and can be easily removed leaving the less buoyant HDL along with other heavier proteins concentrated in the bottom layers. The HDL is then separated from other lipid-free serum proteins by performing a second ultracentrifugation step for 21 hours in d=1.21 g/ml KBr salt solution. The HDL is buoyant in this density salt solution thus at the end of the centrifugation, the upper layers of the gradient contains primarily HDL leaving other plasma proteins in the bottom fraction. This sequential density gradient ultracentrifugation procedure is the "gold standard" for isolation of HDL. However the prolonged time required for both ultracentrifugation steps and the need for multiple density adjustments clearly limits the throughput of the procedure.

SUMMARY OF THE INVENTION

Provided herein are compositions, systems, and methods for extracting and detecting at least one HDL-associated protein (e.g., ApoA1) from a sample (e.g., plasma or serum sample). In certain embodiments, a strong organic acid and hydrophilic organic solvent are mixed with the sample; after centrifugation, the supernatant is transferred to a second container where it is mixed with a non-polar organic solvent; after centrifugation, the lower aqueous layer is transferred to a third container; and then at least a portion of the transferred aqueous layer is subjected to a detection assay such that at least one HDL-associated protein is detected.

In some embodiments, provided herein are methods of extracting and detecting at least one HDL-associated protein comprising: a) mixing, in a first container, a separating solution and a serum or plasma sample to generate a first mixed sample, wherein the separating solution comprises a strong organic acid and a hydrophilic organic solvent, and wherein the separating solution makes up greater than 50% of the first mixed sample; b) exposing the first mixed sample to centrifugal force such that the first mixed sample separates into a pellet and supernatant; c) transferring at least a portion of the supernatant to a second container such that it is separated from the pellet; d) adding a non-polar organic solvent to the second container at a ratio of greater than 1:1 to generate a second mixed sample; e) exposing the second mixed sample to centrifugal force such that the second mixed sample separates into an upper organic solvent layer and a bottom aqueous layer; f) transferring at least a portion of the bottom aqueous layer to a third container such that it is separated from the upper organic solvent layer; and g) subjecting at least a portion of the bottom aqueous layer to a detection assay such that at least one HDL-associated protein is detected.

In additional embodiments, the at least one HDL-associated protein is listed in Table 1. In further embodiments, the at least one HDL-associated protein is human ApoA1. In other embodiments, the mixing in step a) is with a serum sample. In other embodiments, the mixing in step a) is with a plasma sample. In further embodiments, the strong acid is selected from the group consisting of: trifluoroacetic acid, formic acid, acetic acid, pentafluoroproprionic acid, and heptafluorobutryic acid. In other embodiments, the hydrophilic organic solvent is selected from the group consisting of: acetonitrile, methanol, ethanol, propanol, isopropanol, butanol, and tetrahydrofuran. In additional embodiments, the non-polar organic solvent is selected from the group consisting of: hexane, heptane, octane, cyclohexane, methylcyclohexane, and mixtures thereof. In certain embodiments, the separating solution makes up greater than 55% of the first mixed sample (e.g., greater than 60% . . . 75% . . . 87% . . . 93% or more). In other embodiments, the non-polar organic solvent is added to the second container at a ratio of at least 2:1. In other embodiments, the methods further comprise adding a protease and internal standard to the bottom aqueous layer prior to the subjecting to the detection assay.

In some embodiments, the detection assay comprises mass spectrometry. In particular embodiments, the detection assay comprises liquid chromatography. In other embodiments, the detection assay comprises LC-MRM-MS. The present invention is not limited by the methods used to detect HDL-associated proteins. In certain embodiments, the detection method is selected from the following: mass spectrometry, surface plasmon resonance, an in vitro assay, an activity assay, co-immunoprecipitation assay, mass spectrometry, Fluorescence Energy Transfer (FRET), bioluminescence energy transfer (BRET), an immunoassay (e.g., ELISA), interferometry, Biolayer Interferometry (BLI), Dual Polarization Interferometry ("DPI"), Ellipsometry, and Quartz Crystal Microbalance (see, e.g., U.S. Pat. Pub. 20130017556, herein incorporated by reference in its entirety).

In particular embodiments, provided herein are methods comprising: a) mixing a sample with a buffer solution and a pH sensitive protease to generate a mixture, wherein the sample comprises a purified protein, and wherein the pH of the buffer solution changes based on temperature; b) incubating the mixture at a first temperature that causes the buffer to have a first pH, wherein the first pH is in the optimum activity range of the pH sensitive protease such that the pH sensitive protease digests the purified protein generating protein fragments; c) incubating the mixture at a second temperature that causes the buffer to have a second pH, wherein the second pH is outside the optimum activity range of the pH sensitive protease thereby reducing the activity of the pH sensitive protease; and d) subjecting the mixture to a detection method comprising mass spectrometry such that the peptide fragments are detected.

In particular embodiments, the pH sensitive protease is Trypsin, LysC, GluC, ArgC, AspN, Chymotrypsin, Pepsin. In additional embodiments, the purified protein comprises human ApoA1 or other HDL-associated protein. In certain embodiments, the first temperature is about 37 degrees Celsius (e.g., 31-45 degrees Celsius). In other embodiments, the second temperature is about 4 degrees Celsius (e.g., 0-8 degrees Celsius). In some embodiments, the detection method comprises LC-MRM-MS.

DEFINITIONS

Figure 1:
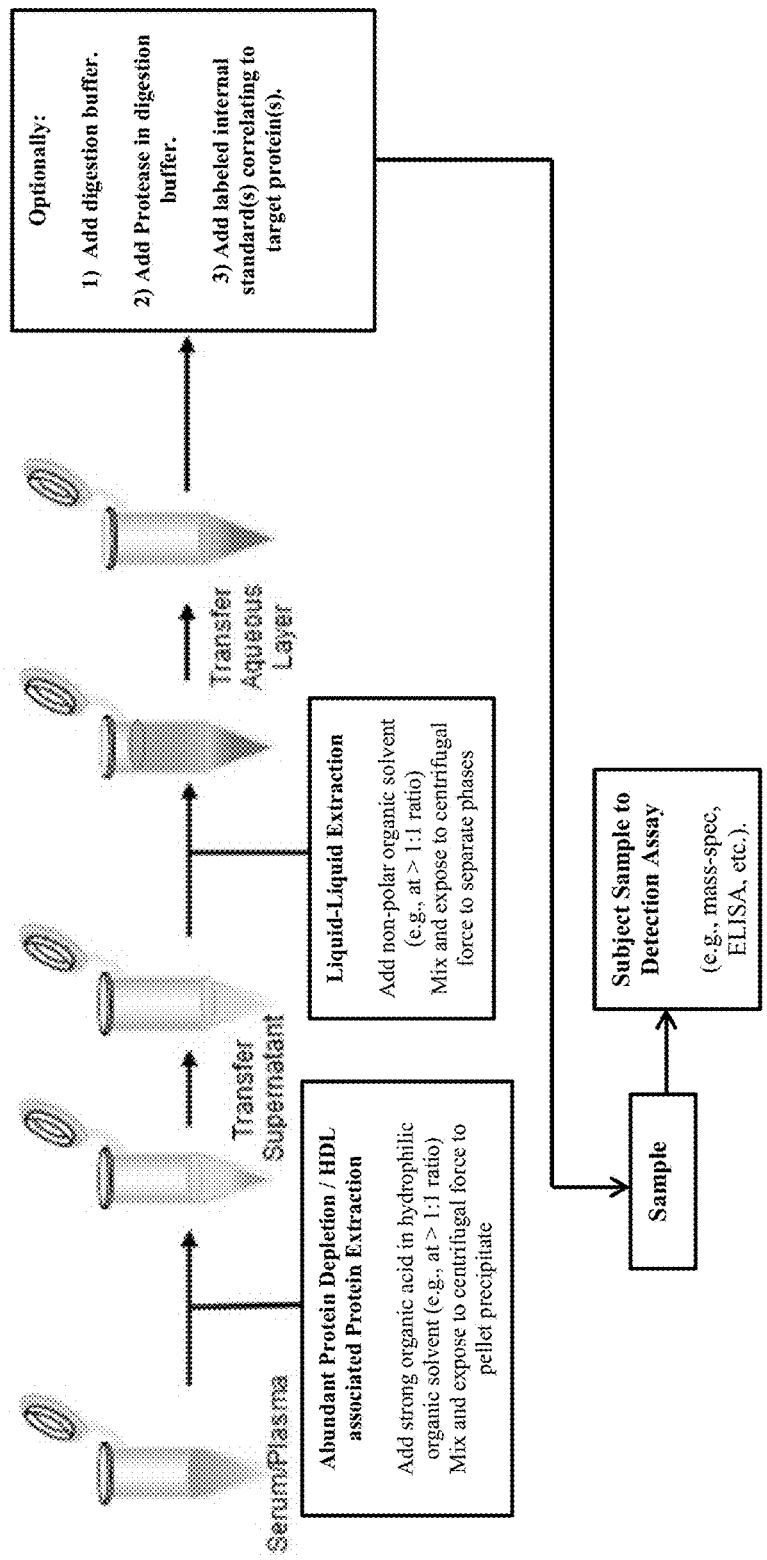
FIG. 1 shows an exemplary embodiment of an HDL-associated protein extraction and detection protocol.

As used herein, "high density lipoprotein" or "HDL" is a circulating, non-covalent assembly of amphipathic proteins that enable lipids like cholesterol and triglycerides to be transported within the water-based bloodstream. HDL is composed of about 50% by mass amphipathic proteins that stabilize lipid emulsions composed of a phospholipid monolayer (about 25%) embedded with free cholesterol (about 4%) and a core of triglycerides (about 3%) and cholesterol esters (about 12%). Subclasses of HDL include HDL2 and HDL3. HDL2 particles are larger and contain a higher content of lipid whereas HDL3 particles are smaller and contain less lipid. Further subclasses include from largest particle to smallest particle, HDL2b, HDL2a, HDL3a, HDL3b, and HDL3c.

As used herein, a "lipoprotein" refers to a type of protein to which one or more lipid molecules is attached or is capable of being attached. In some cases, a lipoprotein may be a "lipid-poor lipoprotein" in which four or fewer molecules of phospholipid are bound. As used herein, a lipoprotein includes a protein to which no lipid is attached but which can be exchanged in an HDL particle (e.g. an apolipoprotein).

As used herein, "sample" refers to a portion of a larger whole to be tested. A sample includes but is not limited to a body fluid such as blood, cerebral spinal fluid, urine, saliva, plasma, serum, and the like.

As used herein, "blood sample" refers to refers to a whole blood sample or a plasma or serum fraction derived therefrom. In certain embodiment, a blood sample refers to a human blood sample such as whole blood or a plasma or serum fraction derived therefrom. In some embodiments, a blood sample refers to a non-human mammalian ("animal") blood sample such as whole blood or a plasma or serum fraction derived therefrom.

As used herein, the term "whole blood" refers to a blood sample that has not been fractionated and contains both cellular and fluid components.

As used herein, "plasma" refers to the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum" as set forth below.

As used herein, the term "serum" refers to whole mammalian serum, such as, for example, whole human serum, whole serum derived from a test animal, whole serum derived from a pet, whole serum derived from livestock, etc. Further, as used herein, "serum" refers to blood plasma from which clotting factors (e.g., fibrinogen) have been removed.

As used herein, the term "strong organic acid" refers to an acid which completely or substantially dissociates in aqueous solution. Stated differently, a strong organic acid is one which has an acidity constant, Ka, of more than about $1 \times 10^{-2}$. The strength of an acid HA in a solvent S is usually defined as being proportional to its acidity constant, i.e., the equilibrium constant Ka for the equilibrium:

$$HA + S \rightleftharpoons A^- + SH^+ \qquad (9)$$

$$K_a = [A^-][SH^+]/[HA] \qquad (10)$$

In equation (10), the constant concentration of the solvent is included in the value for Ka. Since the acidity constant is the ratio of ionized to unionized species, the higher the Ka for a particular organic acid, the greater the extent of the ionization (in a particular solvent system) and the stronger the acid. Examples of such acids include, but are not limited to: trifluoroacetic acid, formic acid, acetic acid, pentafluoroproprionic acid, and heptafluorobutryic acid.

DETAILED DESCRIPTION

Provided herein are compositions, systems, and methods for extracting and detecting at least one HDL-associated protein from a sample (e.g., plasma or serum sample). In certain embodiments, a strong organic acid and hydrophilic organic solvent are mixed with the sample; after centrifugation, the supernatant is transferred to a second container where it is mixed with a non-polar organic solvent; after centrifugation, the lower aqueous layer is transferred to a third container; and then at least a portion of the transferred aqueous layer is subjected to a detection assay such that at least one HDL-associated protein is detected.

In certain embodiments, the purification methods described herein are employed to purify human ApoA1, and particular modified amino acids in ApoA1 (Tyr192 or Trp72) are detected. The myeloperoxidase (MPO)-driven chlorination of apolipoprotein A-I tyrosine 192 (Tyr192) has been shown to be elevated in the presence of vessel wall inflammation, and may serve as a specific biomarker for inflammation associated with cardiometabolic disease (see, Bergt et al. (2004) Proc. Nat. Acad. Sci. U.S.A., 101, 13032-13037; and Shao et al. (2011) J. Biol. Chem., 287, 6375-63861; both of which are herein incorporated by reference). Inflammation mediated oxidation of apolipoprotein A-I has also been shown in the modification of tryptophan 72 (Trp72) to 2-hydroxytryptophan, a.k.a. oxindolylalanine (Oia72) (Huang et al. (2014) Nature Med., 20, 193-203, herein incorporated by reference). Prior work in the field indicates that the modified amino acid residues are present in circulating plasma amount at four to five orders of magnitude less than their unmodified counterparts, presenting a challenge in both detection and quantification. The methods and compositions described herein may be used to quantify low levels of chlorinated Tyr192 (Cl-Tyr192) and Oia72 in apolipoprotein A I relative to amounts of unmodified Tyr192 and Trp72.

Previously, total levels of Cl-Tyr were determined by isolating HDL by sequential ultracentrifugation, delipidating the HDL particles, reducing all of the protein to its amino acid constituents using acid hydrolysis, and quantifying total Cl-Tyr using isotope dilution GC-MS (see, Bergt et al.). Subsequent methodology specifically quantified individual tyrosine residues from ApoA-I by digesting HDL protein with trypsin and quantifying relative amounts of unmodified and modified tyrosine residues from ApoA-I by selected reaction monitoring (SRM) of their tryptic peptides using isotope dilution LC-MS (see, Shao et al.). The detection of ApoA-I Oia72 has previously been accomplished by antibody recognition of HDL isolated from atherosclerotic lesions (see, Huang et al.). Such prior work relies on ultracentrifugation for the isolation of HDL (of which ApoA-I is a major component). Such a method is limited in its capacity to prepare multiple samples in parallel and is time consuming, taking several hours to complete. The use of high amounts of salts and sucrose require that the isolated HDL be further processed before it is in a solution suitable for enzymatic digestion (i.e. trypsin). The use of trypsin as the digesting enzyme on ApoA-I yields abundant missed cleavage fragments that may all contain the targeted residue (i.e, Y192), splitting the signal for a given chemical target amongst several peptide products and having a detrimental effect on assay sensitivity.

Figure 2:
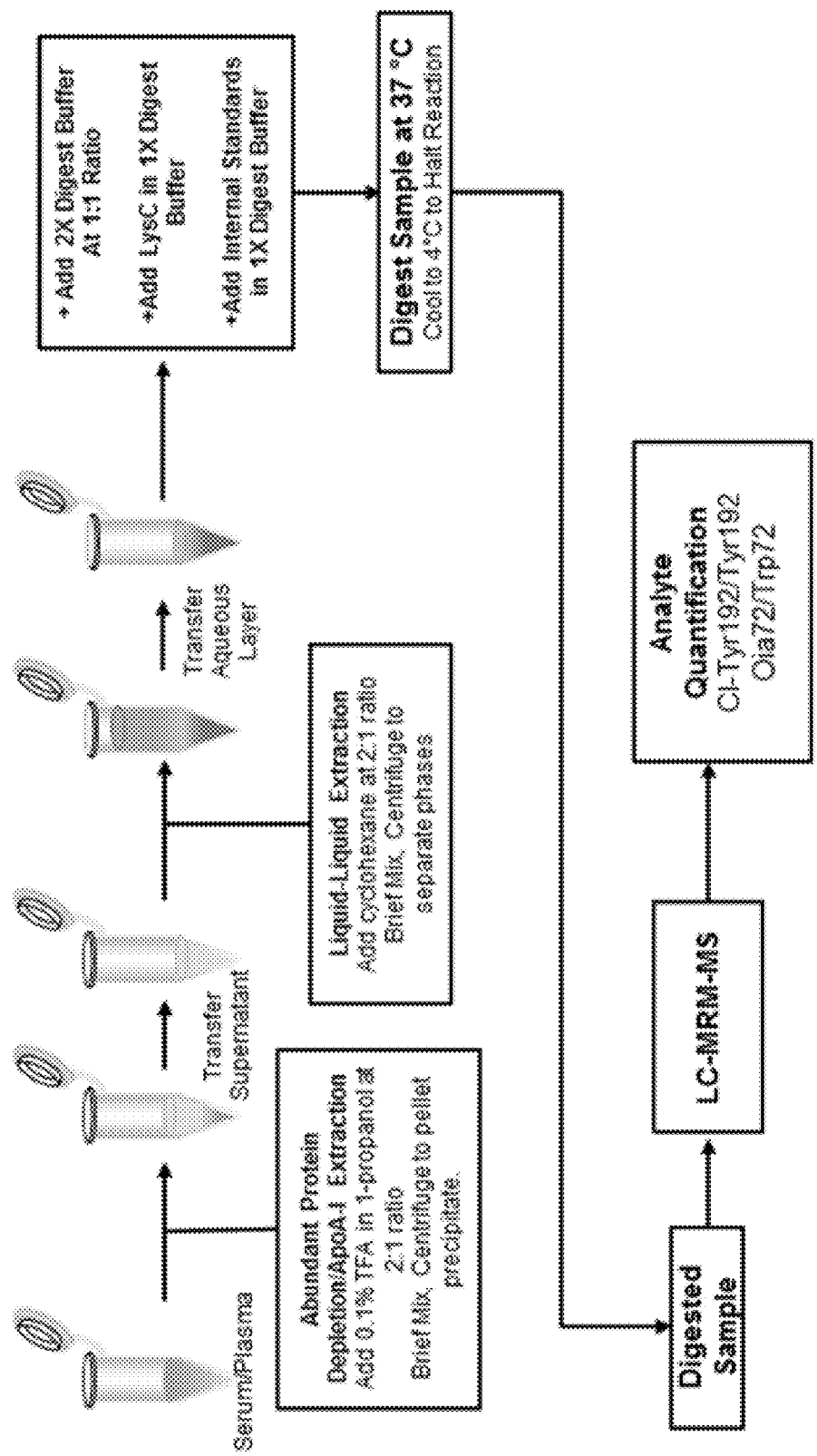
FIG. 2 shows an additional exemplary embodiment of an HDL-associated protein extraction and detection protocol that employs LysC digestion of ApoA1, addition of internal standards, and LC-MRM-MS detection.

FIGS. 1 and 2 show exemplary embodiments of the protein extraction and detection protocol of the present invention. A patient serum or plasma sample is precipitated with the addition of a strong organic acid (e.g., 0.1% trifluoroacetic acid (TFA)) in a hydrophilic organic solvent (e.g., 1-propanol) at a ratio of, for example, 2 to 1. This step depletes the serum of large, abundant proteins (i.e. serum albumin, transferrin, etc.) that could interfere with detection of target peptides downstream. The precipitation is facilitated by brief mixing, after which the precipitate mixture is centrifuged and the supernatant transferred to a new tube. A non-polar organic solvent (e.g., cyclohexane) is added to the hydrophilic organic solvent extract at, for example, a 2:1 ratio, and briefly mixed. The hydrophilic organic solvent and strong organic acid (e.g., 1-propanol and TFA) from the prior extraction are miscible in the non-polar organic solvent (e.g., cyclohexane), while water is immiscible, forming an interface when the mixture is allowed to settle (accelerated by centrifugation). The bottom aqueous layer containing ApoA-I and other HDL associated proteins is then transferred to a new tube. The HDL-associated proteins can then be detected by any appropriate method.

The extraction method described herein can be performed in minutes to prepare a patient sample for enzymatic digest in which ApoA-I is the most abundant protein present and large abundant serum proteins such as serum albumin are not present. The extraction method also can be readily performed in a parallel fashion (i.e. 96-well plates).

The following additional steps, found in FIG. 2, may also be used. Combine the sample 1:1 with a 2× concentrated digestion buffer (e.g., 100 mM Tris-HCl, pH 9.0 (25° C.); 50% methanol) yields the final sample in 1× digest buffer (50 mM Tris-HCl, pH 9.0 (25° C.); 25% methanol). LysC is added to the sample at an approximately 1:20 wt/wt enzyme to substrate ratio (where substrate is protein in the sample) in addition to stable isotope labelled internal standard peptides correlating to the endogenous target peptides for modified and unmodified Tyr192 and Trp72. The sample is then digested at 37° C. and halted by cooling to 4° C., at which point the digested samples are submitted for LC-MRM-MS allowing for the specific detection and quantification of the target peptides. This solution targets two products of inflammation mediated oxidation: chlorinated tyrosine 192 and 2-hydroxy tryptophan 72 in Apolipoprotein A-I. The modified peptides are quantified relative to their correlated unmodified peptides. LysC is used as the enzyme to produce peptide products with no significant missed cleavage products associated with the target amino acid residues. The sequence of the tyrosine 192 containing peptide is:

```
                                        (SEQ ID NO: 1)
        Glu-Asn-Gly-Gly-Ala-Arg-Leu-

Ala-Glu-Tyr/Cl-Tyr-His-Ala-Lys
```

The sequence of the tryptophan containing peptide is:

```
                                        (SEQ ID NO: 2)
        Leu-Arg-Glu-Gln-Leu-Gly-Pro-Val-Thr-Gln-

Glu-Phe-Trp/Oia-Asp-Asn-Leu-Glu-Lys.
```

This protocol uses a specific digestion buffer system to optimize digest pH and peptide/internal standard solubility. In a Tris buffer system, the pH changes with temperature. This solution utilizes a Tris buffer with a pH of 9.00 at 25° C. At 37° C., the pH is 8.70, which is in the optimum range for LysC (pH 8.5-8.8). At 4° C., the pH of the buffer increases to 9.56, which in addition to the decreased temperature is non ideal for the enzyme. The high pH in addition to the 25% methanol in the buffer is optimal to maintain peptide solubility and stability for the Trp72/Oia72 peptides, which are optimum under basic conditions with at least 20% organic content.

The above protocol may employ synthetic peptide internal standards, of which those internal standards correlating to the modified peptide targets (Cl-Tyr192 and Oia72) fully incorporate the desired modification when synthesized, as opposed to performing chemical modifications to unmodified peptide or protein which can result in variation desired product formation.

Using the method in FIG. 2, ApoA-I is rapidly prepared from patient serum/plasma samples in minutes for digestion. The resulting extract is mostly ApoA-I and other HDL-associated proteins, and large, abundant proteins that could interfere with downstream analysis are not present. Digestion with LysC is rapid. With the use of the digestion buffer composition, target peptides are produced at approximately the same rate and reach maximum abundance after about one hour of digestion. Endogenous and stable isotope labelled internal standard peptides containing the target modified and unmodified amino acid residues are readily detected and quantified over 5 orders of magnitude of dynamic range.

The precipitation and extraction procedure outlined in FIG. 2 yields a sample composed of mostly ApoA-I and other HDL-associated proteins. Large, abundant proteins that may suppress ApoA-I signal (i.e. serum albumin) are in low abundance or not detected. (See Table 1)

but with varying termini based on enzyme inefficiencies and limitations. For instance, trypsin digestion of ApoA-I could readily yield 6 peptides that include Tyr192, meaning that one would have to quantify 24 peptide targets to account for Cl-Tyr192, Tyr192, and their corresponding internal standards. Using LysC to digest ApoA-I yields 1 peptide product with no detectable missed cleavage product. The use of LysC also significantly reduces the amount of time to

TABLE 1

Identified Proteins from TFA/Propanol Extracted Serum

| Protein Names | Gene Names | Peptides | Sequence Coverage (%) | Mol. Weight (kDa) | Posterior Error Probability | Intensity | HDL Associated ? |
|---|---|---|---|---|---|---|---|
| Apolipoprotein A-I | APOA1 | 15 | 64 | 30.777 | 6.75E−242 | 1.77E+10 | ✓ 1 |
| Apolipoprotein A-II | APOA2 | 7 | 64 | 11.175 | 1.11E−68 | 5.50E+09 | ✓ 1 |
| Alpha-1-antitrypsin | SERPINA1 | 20 | 54.1 | 45.736 | 0.00E+00 | 1.86E+09 | ✓ 1 |
| Apolipoprotein C-III | APOC3 | 3 | 53.5 | 10.852 | 3.14E−28 | 1.62E+09 | ✓ 1 |
| Apolipoprotein C-I | APOC1 | 4 | 46.8 | 8.647 | 3.11E−23 | 1.43E+09 | ✓ 1 |
| Apolipoprotein A-IV | APOA4 | 15 | 55.8 | 45.398 | 5.51E−218 | 1.28E+09 | ✓ 1 |
| Apolipoprotein C-II | APOC2 | 5 | 56.4 | 11.284 | 1.02E−45 | 9.44E+08 | ✓ 1 |
| Angiotensinogen | AGT | 6 | 25.2 | 53.154 | 3.89E−62 | 2.74E+08 | ✓ 1 |
| Complement C3 | C3 | 9 | 9.4 | 187.15 | 2.85E−118 | 1.40E+08 | ✓ 1 |
| Complement C4-B | C4B | 9 | 6.9 | 187.67 | 2.27E−112 | 8.90E+07 | ✓ 1 |
| Serum amyloid A-4 protein | SAA4 | 2 | 16.2 | 14.746 | 2.28E−05 | 4.86E+07 | ✓ 1 |
| Transthyretin | TTR | 3 | 37.4 | 15.887 | 1.44E−50 | 4.22E+07 | ✓ 1 |
| Pigment epithelium-derived factor | SERPINF1 | 10 | 35.4 | 46.312 | 2.51E−59 | 3.73E+07 | ✓ 1 |
| Apolipoprotein L1 | APOL1 | 9 | 31.3 | 42.158 | 7.86E−43 | 3.68E+07 | ✓ 1 |
| Apolipoprotein F | APOF | 2 | 10.1 | 33.463 | 4.13E−15 | 3.21E+07 | ✓ 1 |
| Hemoglobin subunit beta | HBB | 4 | 30.6 | 15.998 | 3.17E−54 | 2.97E+07 | ✗ 0 |
| Apolipoprotein M | APOM | 2 | 21.8 | 21.253 | 1.32E−14 | 2.71E+07 | ✓ 1 |
| Apolipoprotein C1 | APOC1 | 2 | 29.6 | 5.8348 | 1.67E−07 | 2.48E+07 | ✓ 1 |
| Hemoglobin subunit alpha | HBA1 | 3 | 45.8 | 15.257 | 2.07E−16 | 2.62E+07 | ✗ 0 |
| Fibrinogen alpha chain | FGA | 2 | 5.6 | 69.756 | 9.67E−60 | 2.08E+07 | ✓ 1 |
| Apolipoprotein E | APOE | 5 | 27.1 | 36.154 | 9.83E−55 | 1.52E+07 | ✓ 1 |
| Inter-alpha-trypsin inhibitor heavy chain H4 | ITIH4 | 3 | 4.6 | 79.952 | 2.49E−17 | 1.10E+07 | ✓ 1 |
| Serum amyloid A-1 protein | SAA1 | 1 | 10.7 | 13.532 | 5.96E−04 | 1.06E+07 | ✓ 1 |
| Alpha-2-antiplasmin | SERPINF2 | 7 | 18.7 | 54.565 | 4.09E−52 | 8.41E+06 | ✗ 0 |
| Platelet basic protein activating peptide 2 | PPBP | 3 | 21.1 | 13.894 | 2.46E−10 | 7.88E+06 | ✗ 0 |
| Thyroxine-binding globulin | SERPINA7 | 5 | 16.1 | 46.324 | 4.10E−52 | 6.95E+06 | ✗ 0 |
| Alpha-2-HS-glycoprotein | AHSG | 1 | 2.7 | 39.324 | 9.55E−06 | 3.75E+06 | ✓ 1 |
| Complement C4-A | C4A | 9 | 6.9 | 187.7 | 1.16E−106 | 3.71E+06 | ✓ 1 |
| Beta-2-microglobulin | B2M | 3 | 25.2 | 13.714 | 2.18E−13 | 2.77E+06 | ✗ 0 |
| Complement factor D | CFD | 1 | 6.7 | 27.033 | 1.33E−14 | 2.61E+06 | ✗ 0 |
| Serglycin | SRGN | 1 | 8.2 | 17.652 | 5.79E−09 | 2.37E+06 | ✗ 0 |
| Retinol-binding protein 4 | RBP4 | 2 | 11.1 | 22.944 | 1.50E−06 | 1.87E+06 | ✓ 1 |
| Alpha-2-macroglobulin | A2M | 1 | 20 | 9.7523 | 1.26E−04 | 1.36E+06 | ✗ 0 |
| Apolipoprotein D | APOD | 1 | 5.8 | 21.275 | 1.21E−04 | 1.36E+06 | ✓ 1 |

Sample preparation is more easily accomplished in parallel using the extraction method. It can be performed in multi-well plates and automated by liquid handling robot. Ultracentrifugation severely limits the number of samples that can be simultaneously prepared.

As described above, the extraction protocol may employ Lysyl Endopeptidase (LysC) as the enzyme for digestion of protein into peptides. Digestion with LysC produces single peptides containing target amino acids versus trypsin which produces multiple abundant missed cleavage products that impact sensitivity of measurement. Enzymatic digestion using trypsin is capable of producing multiple missed cleavage products—peptides that contain the target amino acid generate a maximum peptide yield (approximately 1 hour) when compared to trypsin (greater than 18 hours).

Figure 3A:
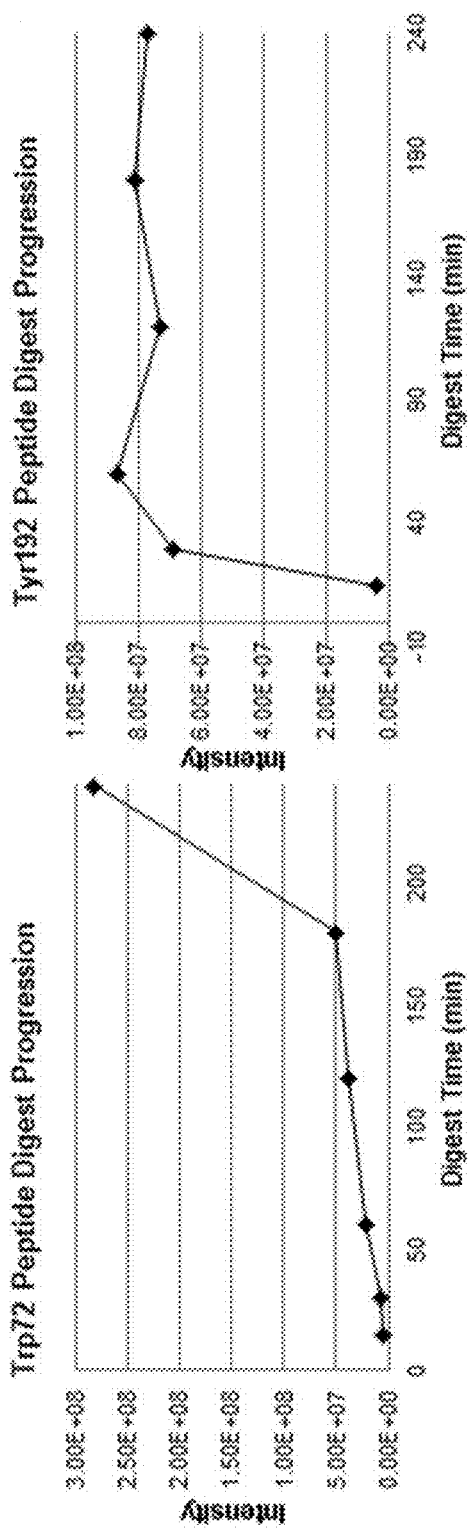
FIGS. 3A-D show the improvement of ApoA-I digestion using the pH-sensitive buffer system described herein.
Figure 3B:
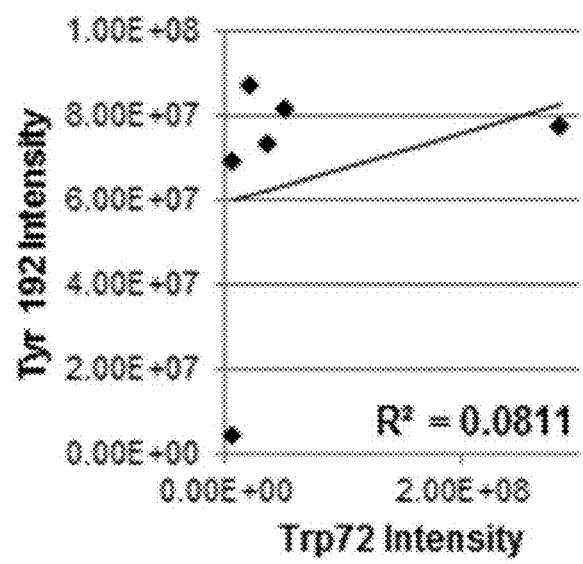
Figure 3D:
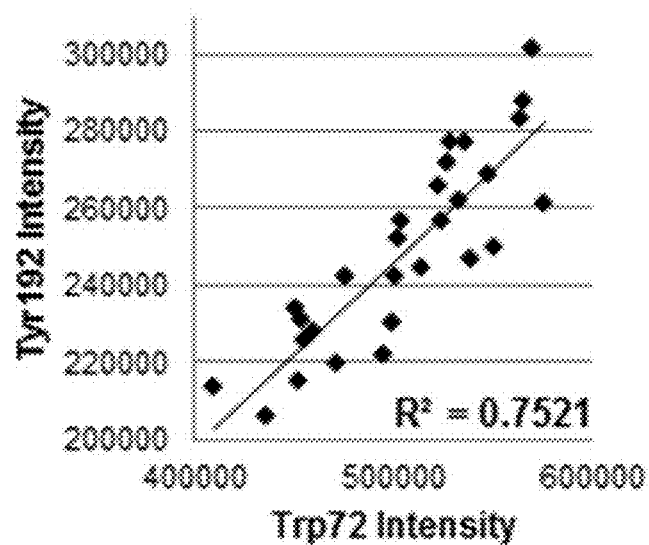
Figure 3C:
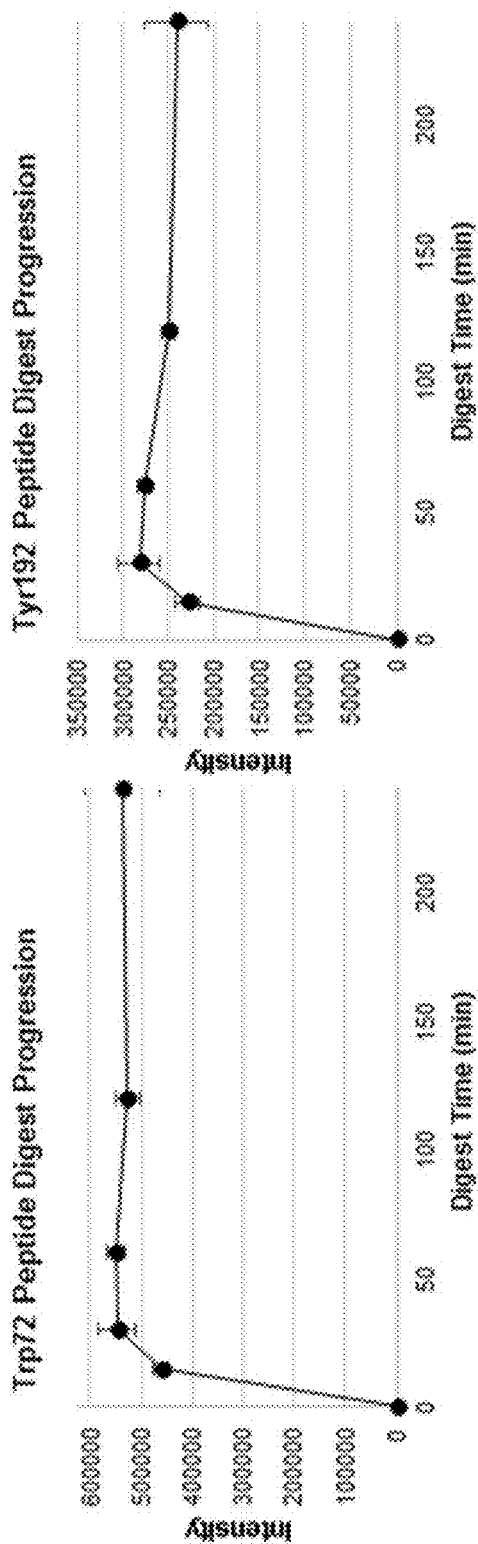

Use of temperature sensitive buffer with some organic solvent content (50 mM Tris-HCl, pH 9.0 (25° C.), 25% Methanol) optimizes pH for digest at 37° in addition to helping hinder enzyme activity at 4° and stabilizing target peptide solubility. Compared to a normal digestion buffer (50 mM Tris, pH 7.8 in Water) (FIGS. 3A and 3B), the target peptides are generated at correlated rates (FIG. 3D) and reach a maximum peptide yield after approximately 1 hour of digestion (FIG. 3C).

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method comprising:
   a) mixing a sample with a buffer solution and a pH sensitive protease to generate a mixture, wherein said sample comprises a purified high density lipoprotein (HDL)-associated protein, and wherein the pH of said buffer solution changes based on temperature;
   b) incubating said mixture at a first temperature that causes said buffer to have a first pH, wherein said first pH is in the optimum activity range of said pH sensitive protease such that said pH sensitive protease digests said purified HDL-associated protein generating protein fragments;
   c) incubating said mixture at a second temperature that causes said buffer to have a second pH, wherein said second pH is outside said optimum activity range of said pH sensitive protease thereby reducing the activity of said pH sensitive protease; and
   d) subjecting said mixture of step c) to a detection method selected from mass spectrometry, liquid chromatography, surface plasmon resonance, an in vitro assay, an activity assay, co-immunoprecipitation assay, Fluorescence Energy Transfer (FRET), bioluminescence energy transfer (BRET), an immunoassay (e.g., ELISA), interferometry, Ellipsometry, and Quartz Crystal Microbalance, such that said peptide fragments are detected, thereby detecting, said purified HDL-associated protein.

2. The method of claim 1, wherein said pH sensitive protease is LysC.

3. The method of claim 1, wherein said purified HDL-associated protein comprises human ApoA1.

4. The method of claim 1, wherein said first temperature is about 30-45 degrees Celsius.

5. The method of claim 1, wherein said second temperature is about 0-8 degrees Celsius.

6. The method of claim 1, wherein said pH sensitive protease is selected from trypsin, LysC, GluC, ArgC, AspN, chymotrypsin, and pepsin.

7. The method of claim 6, wherein said pH sensitive protease is selected from LysC, GluC, ArgC, AspN, chymotrypsin, and pepsin.

8. The method of claim 1, wherein said pH sensitive protease is not trypsin.

9. The method of claim 4, wherein said first temperature is about 37 degrees Celsius.

10. The method of claim 5, wherein said second temperature is about 4 degrees Celsius.

11. The method of claim 1, wherein said purified HDL-associated protein is not purified by a method comprising ultracentrifugation.

12. The method of claim 1, wherein said purified HDL-associated protein is not purified by a method comprising sequential density gradient ultracentrifugation.

13. The method of claim 1, wherein said purified HDL-associated protein comprises one or more of Apolipoprotein A-I (APOAI), Apolipoprotein A-II (ApoA2), Alpha-1-antitrypsin (SERPINA1), Apolipoprotein C-III (AlPOC3), Apolipoprotein C-I (APOCI), Apolipoprotein A-IV (APOA4), Apolipoprotein C-I1 (APOC2), Angiotensinogen (AGT), Complement C3 (C3), Complement C4-B (C4B), Serum amyloid A-4 protein (SAA4), Transthyretin (TTR), Pigment epithelium-derived factor (SERPINF1), Apolipoprotein LI (APOL1), Apolipoprotein F (APOF), Apolipoprotein M (APOM), Apolipoprotein C1 (APOC1), Fibrinogen alpha chain (FGA), Apolipoprotein E (APOE), Inter-alpha-trypsin inhibitor heavy chain H4 (ITIH4), Serum amyloid A-1 protein (SAA1), Alpha-2-HS-glycoprotein (AHSG), Complement C4-A (C4A), Retinol-binding protein 4 (RBP4), and Apolipoprotein D (APOD).

14. The method of claim 1, wherein said detection method comprises mass spectrometry.

15. The method of claim 1, wherein said detection method comprises liquid chromatography.

16. The method of claim 15, wherein said detection method comprises LC-MRM-MS.

* * * * *